(12) United States Patent
Lang (10) Patent No.: US 11,918,026 B2
(45) Date of Patent: Mar. 5, 2024

(54) REDUCING AEROSOL AMMONIA IN HEATED AEROSOL GENERATING ARTICLES

(71) Applicant: PHILIP MORRIS PRODUCTS S.A., Neuchâtel (CH)

(72) Inventor: Gerhard Lang, Neuchâtel (CH)

(73) Assignee: Philip Morris Products S.A., Neuchâtel (CH)

(*) Notice: Subject to any disclaimer, the term of this patent is extended or adjusted under 35 U.S.C. 154(b) by 874 days.

(21) Appl. No.: 16/772,549

(22) PCT Filed: Nov. 21, 2018

(86) PCT No.: PCT/IB2018/059151
§ 371 (c)(1),
(2) Date: Jun. 12, 2020

(87) PCT Pub. No.: WO2019/123048
PCT Pub. Date: Jun. 27, 2019

(65) Prior Publication Data
US 2020/0384221 A1 Dec. 10, 2020

(30) Foreign Application Priority Data
Dec. 21, 2017 (EP) .................... 17209524

(51) Int. Cl.
*A61M 15/06* (2006.01)
*A24B 15/16* (2020.01)
(Continued)

(52) U.S. Cl.
CPC ............ *A24B 15/16* (2013.01); *A24B 15/167* (2016.11); *A24D 1/20* (2020.01); *A61M 15/06* (2013.01); *A61M 2205/3368* (2013.01)

(58) Field of Classification Search
None
See application file for complete search history.

(56) References Cited

U.S. PATENT DOCUMENTS 3,026,226 A 3/1962 Touey et al.
5,076,294 A 12/1991 Kramer
(Continued)

FOREIGN PATENT DOCUMENTS

CN 102355914 A 2/2012
CN 102987564 A 3/2013
(Continued)

OTHER PUBLICATIONS

Chinese Office Action for CN Application No. 201880075954.5 issued by the Chinese Patent Office dated Nov. 29, 2021; 20 pgs. including English translation.
(Continued)

*Primary Examiner* — Dionne W. Mayes
(74) *Attorney, Agent, or Firm* — Mueting Raasch Group (57) ABSTRACT

An aerosol generating article (10) for use with an aerosol generating device includes an aerosol forming substrate (20) an aerosol cooling element (40) and an acid. The article may optionally include one or both of a filter and a support element (30). The aerosol cooling element, the filter, if present, and the support element, if present, are downstream of the aerosol forming substrate. The acid is downstream of the aerosol forming substrate and is positioned to interact with aerosol from the aerosol forming substrate when the aerosol generating article is used with the aerosol generating device. The acid may be in or on one or more of the aerosol cooling element, the filter, and the support element. The acid may selectively remove ammonia from aerosol generated by the article during use.

16 Claims, 2 Drawing Sheets

(51) Int. Cl.
*A24B 15/167* (2020.01)
*A24D 1/20* (2020.01)

(56) References Cited

U.S. PATENT DOCUMENTS

| | | | | |
|---|---|---|---|---|
| 5,161,549 | A * | 11/1992 | Rosario | A24D 3/14 |
| | | | | 131/345 |
| 9,380,810 | B2 | 7/2016 | Rose et al. | |
| 10,952,463 | B2 * | 3/2021 | Minzoni | A24D 3/048 |
| 11,140,916 | B2 * | 10/2021 | Zuber et al. | A24F 42/10 |
| 11,272,731 | B2 * | 3/2022 | Zuber et al. | A24D 1/20 |
| 2015/0313281 | A1 * | 11/2015 | Bonici et al. | A24D 1/22 |
| | | | | 131/330 |

FOREIGN PATENT DOCUMENTS

| | | |
|---|---|---|
| GB | 760 772 A | 11/1956 |
| RU | 2174388 | 10/2001 |
| RU | 2618043 | 5/2017 |
| WO | WO 91/14381 A1 | 10/1991 |
| WO | 1997007771 | 3/1997 |
| WO | WO 2012/164009 A2 | 12/2012 |
| WO | WO 2013/098405 A2 | 7/2013 |
| WO | WO 2013/120565 A2 | 8/2013 |
| WO | WO 2013/131980 A1 | 9/2013 |
| WO | 20130164706 | 11/2013 |
| WO | WO 2013/190036 A1 | 12/2013 |

OTHER PUBLICATIONS

Russian Office Action for RU2020118341 issued by the Patent Office of the Russian Federation dated Apr. 5, 2022; 13 pgs. including English translation.

European Search Report issued by the European Patent Office for corresponding EP Application No. EP17209524.2 dated Jun. 20, 2018; 7 pgs.

International Search Report issued by the European Patent Office for corresponding PCT Application No. PCT/IB2018/059151, dated Feb. 19, 2019; 13 pgs.

International Preliminary Report on Patentability issued by the European Patent Office for corresponding PCT Application No. PCT/IB2018/059151, dated Nov. 15, 2019; 11 pgs.

"Reduction of Mainstream Ammonia for Art Cigarette Models with Filter/Filler Additives," *Analytical Investigation of Tobacco Smoke*, Oct. 1990. Philip Morris U.S.A. Research Center, Richmond, Virginia; 18 pgs.

"Reduction of MS Ammonia of ART cigarettes with Filters Treated with Citric, Malic, and Lactic Acids," Inter-office Correspondence, Philip Morris U.S.A., May 18, 1989; 5 pgs.

* cited by examiner

REDUCING AEROSOL AMMONIA IN HEATED AEROSOL GENERATING ARTICLES

This application is the § 371 U.S. National Stage of International Application No. PCT/IB2018/059151, filed 21 Nov. 2018, which claims the benefit of European Application No. 17209524.2, filed 21 Dec. 2017.

The present disclosure relates to aerosol generating articles and components of such articles that reduce ammonia concentrations in aerosol delivered by the article.

The articles may be used in heat-not-burn aerosol generating devices. Use of aerosol generating articles with heat-not-burn devices avoids combustion and pyrolysis by-products that are delivered in mainstream smoke of combustible smoking articles, such as cigarettes. However, the aerosol generating articles used with heat-not-burn devices deliver similar amounts of nicotine and other volatile components to provide an experience and taste that is similar to combustible smoking articles.

Articles for use with heat-not-burn devices may include tobacco as an aerosol generating substrate. Often the tobacco employed is selected to produce a relatively low concentration of ammonia in aerosol when used with a heat-not-burn device. It would be desirable to provide aerosol generating articles having different taste profiles, including "darker" taste, by using "dark" tobacco types such as Burley. However, such tobaccos tend to produce higher levels of ammonia in the aerosol, which results in a harsh taste.

Articles and processes have been developed to reduce the amount of ammonia delivered in mainstream smoke of combustible smoking articles, such as cigarettes. For example, acids have been incorporated into filters or the tobacco blend of cigarettes. However, the incorporating acids into cigarettes may result in decreased nicotine delivery.

It would be desirable to provide heat-not-burn aerosol generating articles having a broader variety of taste profiles, including tobaccos that tend to produce higher levels of ammonia. It would also be desirable to provide heat-not-burn aerosol generating articles that reduce ammonia levels in delivered aerosol, without substantially reducing nicotine levels.

In various aspects of the present invention, there is provided an aerosol generating article that incorporates acid downstream of an aerosol forming substrate. The acid selectively reduces ammonia levels in the aerosol, without substantially reducing nicotine levels in the aerosol. Acid may be incorporated in or on one or more element of the article, such as an aerosol cooling element, a support element, or a filter. In some embodiments, acid is not incorporated in or on the filter but is incorporated in or on one or both of the aerosol cooling element and the support element. In some embodiments, acid is incorporated in or on an aerosol cooling element, a support element, and a filter. In some embodiments, acid is incorporated in or on the aerosol cooling element and the filter. In some embodiments, acid is incorporated in or on the support element and the filter. In some embodiments where the article includes an aerosol cooling element and a filter, acid is incorporated in or on the filter but not on the aerosol cooling element.

In some aspects of the present invention, there is provided an aerosol generating article for use with an aerosol generating device. The article includes an aerosol forming substrate, an aerosol cooling element, and an acid. The article may optionally include one or both of a filter and a support element. The aerosol cooling element, the filter, if present, and the support element, if present, are downstream of the aerosol forming substrate. The acid is downstream of the aerosol forming substrate and is positioned to interact with aerosol from the aerosol forming substrate when the aerosol generating article is used with the aerosol generating device. The acid may be in or on one or more of the aerosol cooling element, the filter, and the support element. In preferred embodiments, the acid is in or on the filter. Ammonia in aerosol generated from the aerosol forming substrate may be removed by the acid prior to the aerosol being inhaled by a user.

In some aspects of the present invention, there is provided an aerosol cooling element for using an aerosol generating article. The aerosol cooling element comprises a body defining a plurality of longitudinally extending channels and includes an acid in or on the body. The cooling element has a porosity of between 50% and 90% in the longitudinal direction. The acid may selectively remove ammonia from aerosol of the article containing the cooling element.

Various aspects or embodiments of the aerosol generating articles described herein may provide one or more advantages relative to currently available or previously described aerosol generating articles. For example, the taste profile and variety of tobaccos that may be used in aerosol forming substrates of the aerosol generating articles for use with heat-not-burn aerosol generating devices may be improved, because varieties of tobacco that tend to produce higher levels of ammonia in the aerosol may be used due to the ability to reduce ammonia without substantially reducing nicotine. The use of a greater variety of tobaccos may have the added advantage of being more sustainable. In addition, the incorporation of the acid into an element of the article downstream of the aerosol forming substrate, rather than into the aerosol forming substrate, may allow for the tobacco content of the article to be maintained, and not diluted, so that desirable sensorial properties may be maintained and not diluted. Further, the incorporation of acid into an element of the aerosol generating article may reduce harshness of the aerosol delivered to a user due to the removal of ammonia. These and other advantages of various embodiments of the present invention will be readily understood upon reading this disclosure.

Ammonia is a base that may be removed from an aerosol by exposing the aerosol to an element having an acid in or on its surface. As the aerosol contacts the surface of the element, the ammonia may react with the acid to form a non-volatile ammonium salt. Because the ammonium salt is non-volatile, it may be removed from the aerosol. Theoretically, the acid should also react with nicotine, which is also a basic compound, resulting in the removal of nicotine from the aerosol.

Unexpectedly and as described in the Example of the present disclosure, nicotine was not substantially removed from aerosol produced from aerosol generating articles according to embodiments of the present invention when a substrate of the article containing tobacco was heated using a heat-not-burn device. This contrasts with the teachings of PCT published patent application WO 91/14381, in which a cigarette filter that incorporated acids retained the majority of nicotine.

Any suitable acid may be incorporated in or on an element of an aerosol generating article to reduce ammonia. Preferably that acid is sufficiently non-volatile so that most of the acid remains in place on the element and is not transferred into the aerosol during use of the article. For purposes of clarity, the use of "an acid" or "the acid" in the present disclosure refers to "one or more acids." In some embodiments, the acid includes one or more of an organic acid, a carboxylic acid, and a phosphoric acid. For example, the acid may be selected from the group consisting of malic acid, fumaric acid, succinic acid, citric acid, tartaric acid, ascorbic acid, gluconic acid, lactic acid, a saturated fatty acid having a carbon chain length of at least $C_{12}$, and ortho-phosphoric acid.

The acid may be included in a buffer or other suitable composition for application to one or more elements of the aerosol generating article. The composition may comprise a salt of the acid or other suitable component to control the pH of the composition. Selecting an appropriate acid or controlling the pH of the composition applied to the element may allow for more selective removal of ammonia, relative to nicotine, in the aerosol when the article is in use. Ammonia has a pKa of 9.2, while nicotine has a pKa of 8.0. Too strong of an acid or too low of a pH of a composition applied to the element may result in more indiscriminate removal of ammonia and nicotine from the aerosol. Preferably, the pH at the surface of the element once the acid is applied is at least 2 units less than the pKa of ammonia. Preferably, pH at the surface of the element is less than 7.0.

The acid and other components, such as a salt of the acid, if present, may be dissolved in any suitable solvent for application to an element, such as an aerosol cooling element, a filter, or a support element. The choice of solvent may depend on the acid and the element to which the acid is applied. For example, the solvent may be a low solubility solvent that may improve penetration of the acid into the element to which it is applied or to provide a more complete coating of the surface of the element. In some embodiments, the solvent comprises triacetin, glycerine, propylene glycol, triethylcitrate, ethanol, isopropyl alcohol, water, or the like.

The acid may be included in a composition for application to or incorporation into the element of the aerosol generating article in any suitable concentration. For example, the composition may comprise 30% by weight or less of the acid, such as 10% by weight or less of the acid. Preferably, the composition comprises greater than 0.1% of the acid by weight. In some embodiments, the acid is present in the composition at a concentration from about 0.5% to about 10% by weight, such as from about 1% to about 10% by weight. The concentration of the acid may be varied to tailor the amount of ammonia removed from the aerosol.

In some embodiments, solid particles including the acid are applied to, or incorporated in, the element of the aerosol generating article.

The acid may be applied to, or incorporated in, the element in any suitable manner. For example, a composition comprising the acid may be sprayed or printed onto a surface of the element. For example, the compositing may be applied to an inner surface, an outer surface, or both an inner and an outer surface. The entire surface or a portion of the surface may be covered with the composition, depending on the amount of reduction of ammonia and nicotine that is to be removed from the aerosol during use of the aerosol generating article. The composition may be applied to one side or more than one side of the element. The element may be dipped into a composition comprising the acid.

The resulting element with the incorporated acid may have any suitable amount of acid. Preferably, the element comprises less than 10 weight percent of the acid. More preferably, the element comprises less than 5 weight percent of the acid. Typically, the acid will be present in the element at 0.001 weight percent or greater. In some embodiments, the acid is present in the element from about 0.002 wt. % to about 2 wt. %, such as from about 0.004 wt. % to about 1.5 wt %.

If the element is a filter, the weight percent of the acid incorporated into the acid in the filter may be determined based on the weight of the filter material or may be based on the total weight of the filter, which may include, for example, the weight of the filter material, plug wrap, and adhesive. Preferably, the weight percent is determined based on the total weight of the filter.

The amount of acid, Pka of the acid, pH at a surface of an element incorporating the acid, process for incorporation of the acid, and the like may be controlled to achieve a suitable amount of reduction of ammonia from the aerosol, while limiting reduction of nicotine from the aerosol.

Preferably at least 15% of ammonia is removed from aerosol of an aerosol generating article that includes an acid in or on an element that is downstream of the aerosol forming substrate. More preferably, at least 20%, or at least 25%, of ammonia is removed from aerosol of an aerosol generating article having a mouthpiece that includes an acid in or on an element.

Preferably, less than 10% of nicotine is removed from aerosol of an aerosol generating article that includes an acid in or on an element downstream of the aerosol forming substrate. More preferably, less than 6%, or less than 5%, of nicotine is removed from aerosol of an aerosol generating article that includes an acid in or on an element downstream of the aerosol forming substrate. Even more preferably, less than 1% of nicotine is removed from aerosol of an aerosol generating article that includes an acid in or on an element downstream of the aerosol forming substrate. As shown in the Example below, very little to no nicotine was removed from aerosol of an aerosol generating article that included an acid in or on a filter and also included an aerosol cooling element upstream of the filter.

Any suitable test may be employed to determine the amount of ammonia or nicotine removed from aerosol of an aerosol generating article when the article is heated to cause the aerosol forming substrate to produce an aerosol without combusting the substrate. For example, the test articles can be conditioned according to ISO 3402:1999, tested under routine cigarette-smoking machine analytical methods as described in ISO 3308:2012, CORESTA recommended method no. 7 for determination of nicotine and CORESTA recommended method no. 79 for determination of ammonia by ion chromatographic analysis.

In preferred embodiments, the amount of ammonia or nicotine removed from aerosol of the aerosol generating article, in which at least one element downstream of the aerosol forming substrate includes an acid, is determined relative to a substantially similar aerosol generating article in which no element downstream of the aerosol forming substrate includes the acid. The substantially similar aerosol generating article may include all the components of the aerosol generating article in which at least one element includes the acid, except that, in the substantially similar article, the element does not include the acid.

Any suitable element of an aerosol generating article may incorporate an acid to reduce ammonia. One or more elements that incorporate one or more acid may be incorporated into the article such that the elements are downstream of the aerosol generating substrate. The terms "downstream" and "upstream" may be used to describe relative positions of elements or components of the aerosol generating article. For simplicity, the terms "upstream" and "downstream" as used herein refer to a relative position along the length of the aerosol generating article with reference to the direction in which the aerosol is drawn through the article.

The aerosol generating article comprises two ends: a proximal end through which aerosol exits the aerosol generating article and is delivered to a user and a distal end. In use, a user may draw on the proximal end in order to inhale aerosol generated by the aerosol generating article. The proximal end may also be referred to as the mouth end or the downstream end and is downstream of the distal end. The distal end may also be referred to as the upstream end and is upstream of the proximal end.

The one or more elements on or in which the acid is disposed may be included in a mouthpiece of the aerosol generating article. As used herein, a "mouthpiece" refers to a portion of the aerosol generating articles that includes the proximal end of the article. The mouthpiece may be a separate piece of the article or may be integrated as a portion of the article. In some examples, the mouthpiece includes the entire portion of the article downstream aerosol generating substrate. In some examples, the mouthpiece is the portion of the article that includes the aerosol cooling element, the filter if present, and the support element if present.

The aerosol generating article may be assembled in the form of a rod, in which the acid-containing element or mouthpiece comprising the acid-containing element is downstream of the aerosol forming substrate. The acid may be in or on any suitable element, such as one or more of a filter, a support element, and an aerosol cooling element.

Preferably, the aerosol generating article includes an aerosol cooling element. Preferably, the aerosol generating article includes an aerosol cooling element and a filter. In embodiments, where the aerosol generating article is configured to be used with an aerosol generating device in which the device includes a heating element configured to penetrate into the article, the article includes a support element; more preferably, the mouthpiece includes a filter, an aerosol cooling element, and a support element in such embodiments.

In some embodiments, the acid is in or on the filter and the aerosol generating article comprises an aerosol cooling element, which may or may not include an acid, upstream, of the filter.

The aerosol generating article may comprise any suitable aerosol cooling element. Examples of suitable aerosol cooling elements that may be employed in accordance with the teachings presented herein are described in PCT Published Patent Application WO2013/098405 and PCT Published Patent Application WO2013120565.

As used herein, "aerosol-cooling element" refers to a component of an aerosol generating article located downstream of the aerosol forming substrate such that, in use, an aerosol formed by volatile compounds released from the aerosol forming substrate passes through and is cooled by the aerosol cooling element before being inhaled by a user. An aerosol cooling element has a large surface area, but causes a low pressure drop. Filters and other elements that produce a high pressure drop, for example filters formed from bundles of fibres, are not considered to be aerosol cooling elements. Chambers and cavities within an aerosol generating article are not considered to be aerosol cooling elements.

The aerosol cooling element may comprise a plurality of longitudinally extending channels. The aerosol cooling element may have any suitable porosity. For example, the aerosol cooling may have a porosity of between 50% and 90% in the longitudinal direction. The aerosol cooling element may alternatively be referred to as a heat exchanger based on its functionality.

The aerosol cooling element may have any suitable total surface area. For example, the aerosol cooling element may have a total surface area of between 300 $mm^2$ per mm length and 1000 $mm^2$ per mm length. The aerosol cooling element preferably offers a low resistance to the passage of air through the rod. Preferably, the aerosol cooling element does not substantially affect the resistance to draw of the aerosol generating article. Resistance to draw (RTD) is the pressure required to force air through the full length of the object under test at the rate of 17.5 ml/sec at 22° C. and 101 kPa (760 Torr). RTD is typically expressed in units of $mmH_2O$ and is measured in accordance with ISO 6565:2015. Thus, it is preferred that there is a low-pressure drop from an upstream end of the aerosol cooling element to a downstream end of the aerosol cooling element. To achieve this, it is preferred that the porosity in a longitudinal direction is greater than 50% and that the airflow path through the aerosol cooling element is relatively uninhibited. The longitudinal porosity of the aerosol cooling element may be defined by a ratio of the cross-sectional area of material forming the aerosol cooling element and an internal cross-sectional area of the aerosol-generating article at the portion containing the aerosol cooling element.

It is preferred that airflow through the aerosol cooling element does not deviate to a substantive extent between adjacent channels. In other words, it is preferred that the airflow through the aerosol cooling element is in a longitudinal direction along a longitudinal channel, without substantive radial deviation. In some embodiments, the aerosol cooling element is formed from a material that has a low porosity, or substantially no-porosity other than the longitudinally extending channels. That is, the material used to define or form the longitudinally extending channels, for example a crimped and gathered sheet, has low porosity or substantially no porosity.

In some embodiments, the aerosol cooling element may comprise a sheet material selected from the group comprising a metallic foil, a polymeric sheet, and a substantially non-porous paper or cardboard. In some embodiments, the aerosol cooling element may comprise a sheet material selected from the group consisting of polyethylene (PE), polypropylene (PP), polyvinylchloride (PVC), polyethylene terephthalate (PET), polylactic acid (PLA), cellulose acetate (CA), and aluminium foil.

It is desirable that the aerosol cooling element has a high total surface area. Thus, in preferred embodiments the aerosol cooling element is formed by a sheet of a thin material that has been crimped and then pleated, gathered, or folded to form the channels. As used herein, the term 'sheet' denotes a laminar element having a width and length substantially greater than the thickness thereof. As used herein, the term 'crimped' denotes a sheet having a plurality of substantially parallel ridges or corrugations. Preferably, when the aerosol-generating article has been assembled, the substantially parallel ridges or corrugations extend in a longitudinal direction with respect to the rod. As used herein, the terms 'gathered', 'pleated', or 'folded' denote that a sheet of material is convoluted, folded, or otherwise compressed or constricted substantially transversely to the cylindrical axis of the rod. A sheet may be crimped prior to being gathered, pleated or folded. A sheet may be gathered, pleated or folded without prior crimping.

The more folds or pleats within a given volume of the element then the higher the total surface area of the aerosol cooling element. In some embodiments, the aerosol cooling element may be formed from a material having a thickness of between about 5 micrometres and about 500 micrometres, for example between about 10 micrometres and about 250 micrometres. In some embodiments, the aerosol cooling element has a total surface area of between about 300 square millimetres per millimetre of length ($mm^2$/mm) and about 1000 square millimetres per millimetre of length ($mm^2$/mm). In other words, for every millimetre of length in the longitudinal direction the aerosol cooling element may have between about 300 square millimetres and about 1000 square millimetres of surface area. Preferably, the total surface area is about 500 $mm^2$/mm per mm.

The aerosol cooling element may be formed from a material that has a specific surface area of between about 10 square millimetres per milligram ($mm^2$/mg) and about 100 square millimetres per milligram ($mm^2$/mg). In some embodiments, the specific surface area may be about 35 $mm^2$/mg.

Specific surface area can be determined by taking a material having a known width and thickness. For example, the material may be a PLA material having an average thickness of 50 micrometres with a variation of ±2 micrometres. Where the material also has a known width, for example, between about 200 millimetres and about 250 millimetres, the specific surface area and density can be calculated.

When an aerosol that contains a proportion of water vapour is drawn through the aerosol cooling element, some of the water vapour may condense on surfaces of the longitudinally extending channels defined through the aerosol cooling element. If water condenses, it is preferred that droplets of the condensed water are maintained in droplet form on a surface of the aerosol cooling element rather than being absorbed into the material forming the aerosol cooling element. Thus, it is preferred that the material forming the aerosol cooling element is substantially non-porous or substantially non-absorbent to water.

The aerosol cooling element may act to cool the temperature of a stream of aerosol drawn through the element by thermal transfer. Components of the aerosol will interact with the aerosol cooling element and loose thermal energy.

The aerosol cooling element may act to cool the temperature of a stream of aerosol drawn through the element by undergoing a phase transformation that consumes heat energy from the aerosol stream. For example, the material forming the aerosol cooling element may undergo a phase transformation such as melting or a glass transition that requires the absorption of heat energy. If the element is selected such that it undergoes such an endothermic reaction at the temperature at which the aerosol enters the aerosol cooling element, then the reaction will consume heat energy from the aerosol stream.

The aerosol cooling element may act to lower the perceived temperature of a stream of aerosol drawn through the element by causing condensation of components such as water vapour from the aerosol stream. Due to condensation, the aerosol stream may be drier after passing through the aerosol cooling element. In some embodiments, the water vapour content of an aerosol stream drawn through the aerosol cooling element may be lowered by between about 20% and about 90%. The user may perceive the temperature of this aerosol to be lower than a moister aerosol of the same actual temperature. Thus, the feeling of the aerosol in a user's mouth may be closer to the feeling provided by the smoke stream of a conventional cigarette.

In some embodiments, the temperature of an aerosol stream may be lowered by more than 10° C. as it is drawn through an aerosol cooling element. In some embodiments, the temperature of an aerosol stream may be lowered by more than 15° C. or more than 20° C. as it is drawn through an aerosol cooling element. Preferably, the temperature of the aerosol stream is lowered by least about 40° C. or at least about 50° C. as the aerosol stream is drawn through the aerosol cooling element. In some preferred embodiments, the temperature of the aerosol stream entering the aerosol cooling element is about 150° C., and the temperature of the aerosol stream leaving the aerosol cooling element is about 80° C.

As noted above, the aerosol cooling element may be formed from a sheet of suitable material that has been crimped, pleated, gathered or folded into an element that defines a plurality of longitudinally extending channels. A cross-sectional profile of such an aerosol cooling element may show the channels as being randomly oriented. The aerosol cooling element may be formed in any other suitable manner. For example, the aerosol cooling element may be formed from a bundle of longitudinally extending tubes. The aerosol cooling element may be formed by extrusion, molding, lamination, injection, or shredding of a suitable material.

The acid or composition comprising the acid may be added to or disposed on the aerosol cooling element in any suitable manner. For example, the acid or composition may be sprayed, coated, printed or otherwise disposed on a sheet that may form the element prior to the sheet being crimped, pleated, gathered, or folded into the aerosol cooling element. In addition or alternatively, the acid or composition may be disposed on the aerosol cooling element after the element is formed. In addition or alternatively, the acid or composition may be incorporated into the material forming the sheet or material that is extruded, molded, laminated, injected, or shredded to form the aerosol cooling element.

The aerosol cooling element may comprise an outer tube or wrapper that contains or locates the longitudinally extending channels. For example, a pleated, gathered, or folded sheet material may be wrapped in a wrapper material, for example a plug wrapper, to form the aerosol cooling element. In some embodiments, the aerosol cooling element comprises a sheet of crimped material that is gathered into a rod-shape and bound by a wrapper, for example a wrapper of filter paper.

The outer tube or wrapper may incorporate the acid, or the acid may be disposed on the outer tube or wrapper, such as an inner surface of the outer tube or wrapper.

In some embodiments, the aerosol cooling element is formed in the shape of a rod having a length of between about 7 millimetres (mm) and about 28 millimetres (mm). For example, an aerosol cooling element may have a length of about 18 mm. In some embodiments, the aerosol cooling element may have a substantially circular cross-section and a diameter of about 5 mm to about 10 mm. For example, an aerosol-cooling element may have a diameter of about 7 mm.

The aerosol generating article may optionally comprise support element. The article may comprise any suitable support element. Examples of suitable support elements that may be employed in accordance with the teachings presented herein are described in PCT Published Patent Application WO2013/098405.

The aerosol generating article preferably comprises a support element when the article is configured for use with an aerosol generating device that includes a heating element configured to penetrate the article. Preferably, the support element, when present, abuts the aerosol forming substrate such that the support element is located immediately downstream of the aerosol forming substrate in the aerosol generating article. The support element may provide support to the article and the upstream aerosol forming substrate to resist forces associated with one or both of penetration of the heating element into the article or insertion of the article into the device.

In preferred embodiments, the support element is configured to resist downstream movement of the aerosol forming substrate during insertion of the heating element of the aerosol generating device into the aerosol forming substrate of aerosol generating article.

In some embodiments, the support element is configured to resist a penetration force of at least 2.5 N during insertion of a heating element of an aerosol-generating device into the aerosol forming substrate. Preferably the support element is configured to resist a penetration force of at least 4 N during insertion of a heating element of an aerosol-generating device into the aerosol forming substrate. As used herein, the term 'penetration force' is used to describe the maximum insertion force during insertion of the heating element into the aerosol forming substrate of the aerosol generating article and prior to the aerosol-generating article reaching a position of maximum insertion.

Preferably, the support element has a fracture force of at least 40 N, for example at least 45 N or at least 50 N as measured using a standard compression test.

The support element may be formed from any suitable material or combination of materials. For example, the support element may be formed from one or more materials selected from the group consisting of: cellulose acetate; cardboard; crimped paper, such as crimped heat resistant paper or crimped parchment paper; and polymeric materials, such as low-density polyethylene (LDPE). In a preferred embodiment, the support element is formed from cellulose acetate.

The support element may comprise a hollow tubular element. In a preferred embodiment, the support element comprises a hollow cellulose acetate tube. The support element preferably has an external diameter that is approximately equal to the external diameter of the aerosol generating article.

The support element may have an external diameter of between approximately 5 millimetres and approximately 12 millimetres, for example of between approximately 5 millimetres and approximately 10 millimetres or of between approximately 6 millimetres and approximately 8 millimetres. In a preferred embodiment, the support element has an external diameter of 7.2 millimetres+1-10%.

The support element may have a length of between approximately 5 millimetres and approximately 15 mm. In a preferred embodiment, the support element has a length of approximately 8 millimetres.

The aerosol generating article may optionally comprise a filter. The filter, if present, is preferably located at the proximal, mouth end of the aerosol generating article. The article may comprise any suitable filter. Examples of suitable filter material include cellulose esters such as cellulose acetate, polylactic acid (PLA), cellulosic material, polypropylene, cotton, flax, hemp, or any degradable filtration media, or a combination or blend of any two or more of filter materials. In preferred embodiments, the filter material includes polymeric filter material such as polylactic acid, cellulose esters, and blends thereof. Preferably, the filter material includes a cellulose ester. Examples of cellulose esters that can be used to form filter material include cellulose acetates, cellulose propionates and cellulose butyrates with varying degrees of substitution, as well as mixed esters thereof. Examples of such mixed esters include cellulose acetate propionate, cellulose acetate butyrate, and cellulose acetate propionate butyrate. Preferably, the filter material comprises cellulose acetate. More preferably, the filter comprises a cellulose acetate tow filer of low filtration efficiency.

The filter material preferably includes fibres. Preferably, the filter material comprises a fibrous polymeric filter material. In preferred embodiments, the filter material comprises cellulose acetate fibres or polylactic acid fibres. In preferred embodiments, the filter material includes fibres or bundles of fibres in the form of a tow band.

A filter may include one or more optional binding agents. Preferably, a filter that includes a binding agent comprises polymeric fibres. The binding agent can bind the polymeric fibres together. Preferably, the binding agent, if included, is a plasticizer. As used herein, a "plasticizer" is a solvent, that when applied to polymeric fibres, solvent-bonds the fibres together. Examples of plasticizers include triacetin (also known as glycerol triacetate), diethylene glycol diacetate, triethylene glycol diacetate, tripropion, acetyl triethyl citrate, triethyl citrate and mixtures of one or more thereof. One or more plasticizers may be mixed with, for example, polyethylene glycol and contacted with the polymeric fibres to solvent-bond the fibres together. The fibres may be contacted with a binding agent in any suitable manner. Preferably, a composition comprising the binding agent is sprayed on the polymeric fibres.

The acid may be included in or applied to the filter in any suitable manner. For example, the filter material may be dipped in a solution comprising the acid; the acid may be sprayed, printed, coated, or otherwise disposed on the filter material; the acid may be incorporated into the material forming the filter; of the like. In some embodiments, the acid may be included in the composition comprising the binding agent for spraying on the fibres.

Filters of the present invention may have any suitable dimensions. The filter preferably has an external diameter that is approximately equal to the external diameter of the aerosol-generating article. The filter preferably has an external diameter of at least 5 millimetres. The filter may have an external diameter of between approximately 5 millimetres and approximately 12 millimetres, for example of between approximately 5 millimetres and approximately 10 millimetres or of between approximately 6 millimetres and approximately 8 millimetres. In a preferred embodiment, the filter has an external diameter of 7.2 millimetres+/-10%.

The filter may have any suitable length. Preferably the filter has a length in a range from about 2 mm to about 15 mm, such as from about 5 mm to about 10 mm. In a preferred embodiment, the filter has a length of about 7 mm.

The aerosol generating article may include any suitable aerosol generating substrate. Preferably, the aerosol forming substrate is a solid aerosol forming substrate. The aerosol forming substrate may comprise both solid and liquid components. Preferably, the aerosol forming substrate comprises nicotine. More preferably, the aerosol forming substrate comprises tobacco. Alternatively or in addition, the aerosol forming substrate may comprise a non-tobacco containing aerosol forming material.

If the aerosol forming substrate is a solid aerosol forming substrate, the solid aerosol forming substrate may comprise, for example, one or more of: powder, granules, pellets, shreds, strands, strips or sheets containing one or more of: herb leaf, tobacco leaf, tobacco ribs, expanded tobacco and homogenised tobacco.

Optionally, the solid aerosol-forming substrate may contain tobacco or non-tobacco volatile flavour compounds, which are released upon heating of the solid aerosol forming substrate. The solid aerosol forming substrate may also contain one or more capsules that, for example, include additional tobacco volatile flavour compounds or non-tobacco volatile flavour compounds and such capsules may melt during heating of the solid aerosol-forming substrate.

Optionally, the solid aerosol-forming substrate may be provided on or embedded in a thermally stable carrier. The carrier may take the form of powder, granules, pellets, shreds, strands, strips or sheets. The solid aerosol-forming substrate may be deposited on the surface of the carrier in the form of, for example, a sheet, foam, gel or slurry. The solid aerosol-forming substrate may be deposited on the entire surface of the carrier, or alternatively, may be deposited in a pattern in order to provide a non-uniform flavour delivery during use.

In a preferred embodiment, the aerosol forming substrate comprises homogenised tobacco material. As used herein, the term 'homogenised tobacco material' denotes a material formed by agglomerating particulate tobacco.

Preferably, the aerosol forming substrate comprises a gathered sheet of homogenised tobacco material. As used herein, the term 'sheet' denotes a laminar element having a width and length substantially greater than the thickness thereof. As used herein, the term 'gathered' is used to describe a sheet that is convoluted, folded, or otherwise compressed or constricted substantially transversely to the longitudinal axis of the aerosol-generating article.

In a preferred embodiment, the aerosol forming substrate comprises a gathered textured sheet of homogenised tobacco material. As used herein, the term 'textured sheet' denotes a sheet that has been crimped, embossed, debossed, perforated or otherwise deformed. The aerosol forming substrate may comprise a gathered textured sheet of homogenised tobacco material comprising a plurality of spaced-apart indentations, protrusions, perforations or a combination thereof.

In a particularly preferred embodiment, the aerosol forming substrate comprises a gathered crimped sheet of homogenised tobacco material. As used herein, the term 'crimped sheet' denotes a sheet having a plurality of substantially parallel ridges or corrugations. Preferably, when the aerosol generating article has been assembled, the substantially parallel ridges or corrugations extend along or parallel to the longitudinal axis of the aerosol generating article. However, it will be appreciated that crimped sheets of homogenised tobacco material for inclusion in the aerosol generating article may alternatively or in addition have a plurality of substantially parallel ridges or corrugations that are disposed at an acute or obtuse angle to the longitudinal axis of the aerosol generating article when the aerosol generating article has been assembled.

In certain embodiments, the aerosol forming substrate may comprise a gathered sheet of homogenised tobacco material that is substantially evenly textured over substantially its entire surface. For example, the aerosol forming substrate may comprise a gathered crimped sheet of homogenised tobacco material comprising a plurality of substantially parallel ridges or corrugations that are substantially evenly spaced-apart across the width of the sheet.

The aerosol forming substrate may be in the form of a plug comprising an aerosol forming material circumscribed by a paper or other wrapper. Where an aerosol forming substrate is in the form of a plug, the entire plug including any wrapper is considered to be the aerosol forming substrate. In a preferred embodiment, the aerosol forming substrate comprises a plug comprising a gathered textured sheet of homogenised tobacco material circumscribed by a wrapper. In a particularly preferred embodiment, the aerosol forming substrate comprises a plug comprising a gathered crimped sheet of homogenised tobacco material circumscribed by a wrapper.

In certain embodiments, sheets of homogenised tobacco material for use in the aerosol forming substrate may have a tobacco content of approximately 70% or more by weight on a dry weight basis.

Sheets of homogenised tobacco material for use in the aerosol forming substrate may comprise one or more intrinsic binders, that is tobacco endogenous binders, one or more extrinsic binders, that is tobacco exogenous binders, or a combination thereof to help agglomerate the particulate tobacco. Alternatively, or in addition, sheets of homogenised tobacco material for use in the aerosol forming substrate may comprise other additives including, but not limited to, tobacco and non-tobacco fibres, aerosol-formers, humectants, plasticisers, flavourants, fillers, aqueous and non-aqueous solvents and combinations thereof.

Suitable extrinsic binders for inclusion in sheets of homogenised tobacco material for use in the aerosol forming substrate are known in the art and include, but are not limited to: gums such as, for example, guar gum, xanthan gum, arabic gum and locust bean gum; cellulosic binders such as, for example, hydroxypropyl cellulose, carboxymethyl cellulose, hydroxyethyl cellulose, methyl cellulose and ethyl cellulose; polysaccharides such as, for example, starches, organic acids, such as alginic acid, conjugate base salts of organic acids, such as sodium-alginate, agar and pectins; and combinations thereof.

Suitable non-tobacco fibres for inclusion in sheets of homogenised tobacco material for use in the aerosol-generating substrate are known in the art and include, but are not limited to: cellulose fibers; soft-wood fibres; hard-wood fibres; jute fibres and combinations thereof. Prior to inclusion in sheets of homogenised tobacco material for use in the aerosol-generating substrate, non-tobacco fibres may be treated by suitable processes known in the art including, but not limited to: mechanical pulping; refining; chemical pulping; bleaching; sulfate pulping; and combinations thereof.

Sheets of homogenised tobacco material for use in the aerosol forming substrate should have sufficiently high tensile strength to survive being gathered to form the aerosol forming substrate. In certain embodiments non-tobacco fibres may be included in sheets of homogenised tobacco material for use in the aerosol forming substrate in order to achieve an appropriate tensile strength.

For example, homogenised sheets of tobacco material for use in the aerosol forming substrate may comprise between approximately 1% and approximately 5% non-tobacco fibres by weight on a dry weight basis.

Preferably, the aerosol forming substrate comprises an aerosol former. As used herein, the term 'aerosol former' is used to describe any suitable known compound or mixture of compounds that, in use, facilitates formation of an aerosol and that is substantially resistant to thermal degradation at the operating temperature of the aerosol-generating article.

Suitable aerosol-formers are known in the art and include, but are not limited to: polyhydric alcohols, such as propylene glycol, triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate Preferred aerosol formers are polyhydric alcohols or mixtures thereof, such as propylene glycol, triethylene glycol, 1,3-butanediol and, most preferred, glycerine.

The aerosol-forming substrate may comprise a single aerosol former. Alternatively, the aerosol-forming substrate may comprise a combination of two or more aerosol formers.

Preferably, the aerosol forming substrate has an aerosol former content of greater than 5% on a dry weight basis. The aerosol forming substrate may have an aerosol former content of between approximately 5% and approximately 30% on a dry weight basis. In a preferred embodiment, the aerosol-forming substrate has an aerosol former content of approximately 20% on a dry weight basis.

Aerosol-forming substrates comprising gathered sheets of homogenised tobacco for use in the aerosol-generating article may be made by methods known in the art, for example the methods disclosed in WO 2012/164009 A2.

In a preferred embodiment sheets of homogenised tobacco material for use in the aerosol generating article are formed from a slurry comprising particulate tobacco, guar gum, cellulose fibres and glycerine by a casting process.

The aerosol forming element preferably has an external diameter that is approximately equal to the external diameter of the aerosol-generating article.

Preferably, the aerosol forming substrate has an external diameter of at least 5 millimetres. The aerosol-forming substrate may have an external diameter of between approximately 5 millimetres and approximately 12 millimetres, for example of between approximately 5 millimetres and approximately 10 millimetres or of between approximately 6 millimetres and approximately 8 millimetres. In a preferred embodiment, the aerosol-forming substrate has an external diameter of 7.2 millimetres+/−10%.

The aerosol forming substrate may have a length of between approximately 7 millimetres and approximately 15 mm. In one embodiment, the aerosol-forming substrate may have a length of approximately 10 millimetres. In a preferred embodiment, the aerosol-forming substrate has a length of approximately 12 millimetres.

The aerosol generating articles may be assembled in any suitable manner. Preferably, the aerosol cooling element is placed downstream of an aerosol forming substrate, and the aerosol cooling element and the aerosol forming substrate are circumscribed by an outer wrapper. Any suitable outer wrapper may be employed. For example, the outer wrapper may be a cigarette paper or other suitable materials well known in the art. The outer wrapper may grip the components of the aerosol generating article when the article is assembled and hold them in position within a rod.

If the aerosol generating article includes a filter, the filter may be downstream of the aerosol cooling element and circumscribed by the outer wrapper. If the aerosol generating article comprises the support element, the support element may be between the aerosol cooling element and the aerosol forming substrate and may be circumscribed by the outer wrapper. Preferably, the support element, if present, is located immediately downstream of the aerosol forming substrate and abuts the aerosol forming substrate.

In embodiments where the aerosol generating article is configured for use with an aerosol generating element that includes a heating element configured to penetrate the aerosol forming substrate, the aerosol generating article preferably includes a support element.

The aerosol generating article may optionally comprise a front plug upstream of the aerosol forming substrate. The front plug, if present, may be located at the upstream end of the aerosol-generating article. The front plug may prevent egress of the aerosol forming substrate from the upstream end of the aerosol forming substrate during handling and shipping.

The front plug may be configured to prevent egress of the aerosol forming substrate from the aerosol generating article during use, for example as a heating element of an aerosol generating device is withdrawn from the aerosol generating article. Alternatively or in addition, the front-plug may be configured to wipe a surface of the heating element of the aerosol generating device as the heating element of the aerosol generating device is withdrawn from the aerosol generating article. The front-plug may define a hole or slit through which a heating element of an aerosol-generating device can pass. Alternatively, the front-plug may be formed of a pierceable material if the article is configured to be used with an aerosol generating device that includes a heating element configured to penetrate the aerosol forming substrate of the article.

The front-plug may be made from an air permeable material that allows air to be drawn through the front plug. In such embodiments, a user may draw air downstream through the aerosol generating article through the front-plug. For example, the front plug may be formed from an air permeable filter material, such as the materials of the optional filter described above.

Alternatively, the front plug may be formed from an air impermeable material. In such embodiments, the aerosol-generating article may further comprise one or more air inlets downstream of the front plug through which air may be drawn into the aerosol generating article.

The front plug, if present, preferably has an external diameter that is approximately equal to the external diameter of the aerosol-generating article. The front plug, if present, preferably has an external diameter of at least 5 millimetres. The front plug may have an external diameter of between approximately 5 millimetres and approximately 12 millimetres, for example of between approximately 5 millimetres and approximately 10 millimetres or of between approximately 6 millimetres and approximately 8 millimetres. In a preferred embodiment, the front plug has an external diameter of 7.2 millimetres+/−10%.

The front plug, if present, preferably the front plug has a length of at least 2 millimetres, more preferably at least 3 millimetres or at least 4 millimetres. The front-plug may have a length of between approximately 2 millimetres and approximately 10 mm, for example of between approximately 4 millimetres and approximately 8 mm.

As used herein, the term ‘diameter’ is used to describe the maximum dimension in the transverse direction of the aerosol-generating article. As used herein, the term ‘length’ is used to describe the maximum dimension in the longitudinal direction of the aerosol-generating article.

As used herein, the term ‘longitudinal’ is used to describe the direction between the downstream end and the upstream end of the aerosol-generating article and the term ‘transverse’ is used to describe the direction perpendicular to the longitudinal direction.

The aerosol generating article may have any suitable dimensions. For example, the aerosol generating article may have a total length between approximately 30 mm and approximately 100 mm. In some embodiments, the aerosol generating article has a total length of approximately 45 mm.

The aerosol generating article may have an external diameter between approximately 5 mm and approximately 12 mm. In some embodiments, the aerosol generating article has an external diameter of approximately 7.2 mm.

Reference will now be made to the drawings, which depict one or more aspects described in this disclosure. However, it will be understood that other aspects not depicted in the drawings fall within the scope and spirit of this disclosure. Like numbers used in the figures refer to like components, steps and the like. However, it will be understood that the use of a number to refer to a component in a given figure is not intended to limit the component in another figure labeled with the same number. In addition, the use of different numbers to refer to components in different figures is not intended to indicate that the different numbered components cannot be the same or similar to other numbered components. The figures are presented for purposes of illustration and not limitation. Schematic drawings presented in the figures are not necessarily to scale.

Figure 1:
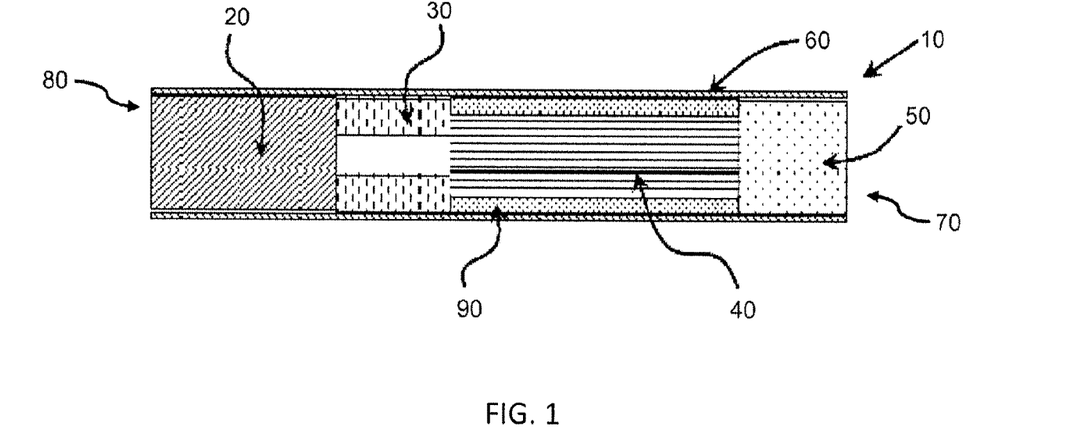
FIG. 1 is a schematic cross-sectional diagram of an embodiment of an aerosol-generating article for use with an aerosol generating-device comprising a heating element.

FIG. 1 illustrates an aerosol generating article 10 according to an embodiment. The aerosol generating article 10 comprises four components arranged in coaxial alignment: an aerosol forming substrate 20, a support element 30, an aerosol cooling element 40, and a filter 50. These four components are arranged sequentially and are circumscribed by an outer wrapper 60 to form the aerosol generating article 10. The aerosol generating 10 has a proximal or mouth end 70, which a user inserts into his or her mouth during use, and a distal end 80 located at the opposite end of the aerosol generating article 10 to the mouth end 70.

An acid is in or on at least one of the support element 30, the aerosol cooling element 40, and the filter 50. In some embodiments, the acid is on or in at least the aerosol cooling element 40. In some embodiments, the acid is on or in at least the filter 50.

In use air is drawn through the aerosol generating article by a user from the distal end 80 to the mouth end 70. The distal end 80 of the aerosol generating article may also be described as the upstream end of the aerosol generating article 10 and the mouth end 70 of the aerosol generating article 10 may also be described as the downstream end of the aerosol generating article 10. Elements of the aerosol generating article 10 located between the mouth end 70 and the distal end 80 may be described as being upstream of the mouth end 70 or, alternatively, downstream of the distal end 80.

The aerosol forming substrate 20 is located at the extreme distal or upstream end of the aerosol-generating article 10. In the embodiment illustrated in FIG. 1, aerosol forming substrate 20 comprises a gathered sheet of crimped homogenised tobacco material circumscribed by a wrapper. The crimped sheet of homogenised tobacco material comprises comprising glycerine as an aerosol-former.

The support element 30 is located immediately downstream of the aerosol forming substrate 20 and abuts the aerosol forming substrate 20. In the embodiment shown in FIG. 1, the support element 30 is a hollow cellulose acetate tube. The support element 30 locates the aerosol forming substrate 20 at the extreme distal end 80 of the aerosol generating article 10 so that it may be penetrated by a heating element of an aerosol generating device. The support element 30 acts to prevent the aerosol forming substrate 20 from being forced downstream within the aerosol generating article 10 towards the aerosol cooling element 40 when a heating element of an aerosol generating device is inserted into the aerosol forming substrate 20. The support element 30 also acts as a spacer to space the aerosol-cooling element 40 of the aerosol generating article 10 from the aerosol forming substrate 20.

The aerosol cooling element 40 is located immediately downstream of the support element 30 and abuts the support element 30. In use, volatile substances released from the aerosol forming substrate 20 pass along the aerosol cooling element 40 towards the mouth end 70 of the aerosol generating article 10. The volatile substances may cool within the aerosol cooling element 40 to form an aerosol that is inhaled by the user. In the embodiment illustrated in FIG. 1, the aerosol cooling element comprises a crimped and gathered sheet of polylactic acid circumscribed by a wrapper 90. The crimped and gathered sheet of polylactic acid defines a plurality of longitudinal channels that extend along the length of the aerosol cooling element 40.

The filter 50 is located immediately downstream of the aerosol cooling element 40 and abuts the aerosol cooling element 40. In the embodiment illustrated in FIG. 1, the filter 50 comprises a conventional cellulose acetate tow filter of low filtration efficiency.

To assemble the aerosol generating article 10, the four components described above are aligned and tightly wrapped within the outer wrapper 60. In the embodiment illustrated in FIG. 1, the outer wrapper 60 is a conventional cigarette paper. As shown in FIG. 1, an optional row of perforations is provided in a region of the outer wrapper 60 circumscribing the support element 30 of the aerosol generating article 10.

In the embodiment illustrated in FIG. 1, a distal end portion of the outer wrapper 60 of the aerosol-generating article 10 is circumscribed by a band of tipping paper (not shown).

The aerosol-generating article 10 illustrated in FIG. 1 is designed to engage with an aerosol generating device comprising a heating element in order to be consumed by a user. In use, the heating element of the aerosol generating device heats the aerosol forming substrate 20 of the aerosol generating article 10 to a sufficient temperature to form an aerosol, which is drawn downstream through the aerosol generating article 10 and inhaled by the user.

As the aerosol passes the support element 30, the aerosol cooling element 40, and the filter 50, one or in at least one of which the acid is disposed, at least some of the ammonia in the aerosol interacts with the acid and is removed from the aerosol prior passing the mouth end 70 for inhalation by a user.

Figure 2:
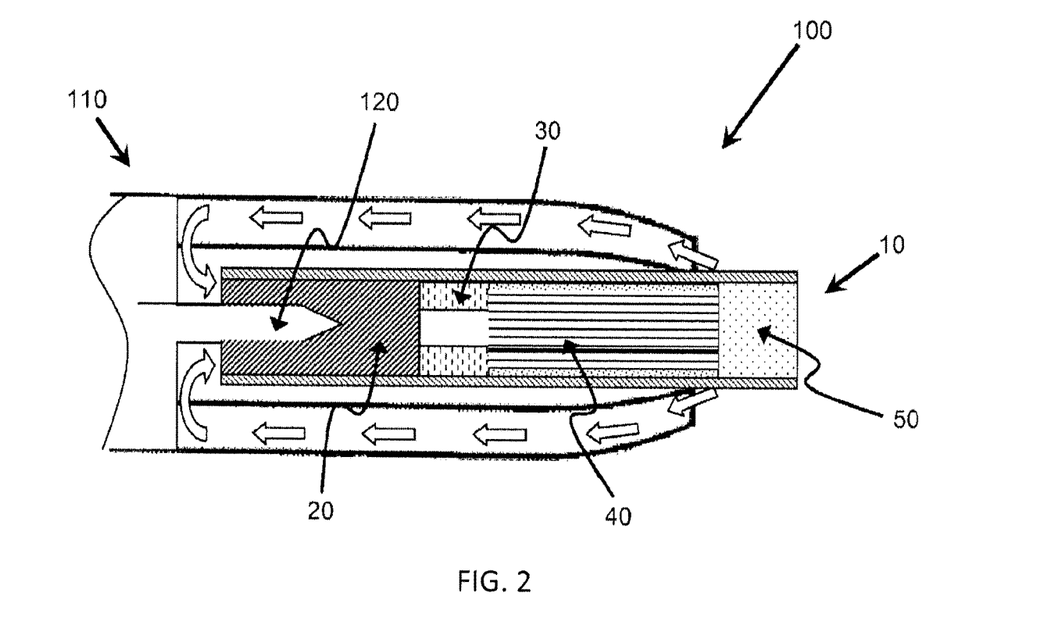
FIG. 2 is a schematic cross-sectional diagram of an embodiment of an aerosol-generating system comprising an electrically heated aerosol-generating device comprising a heating element and an aerosol-generating article according to the embodiment illustrated in FIG. 1.

FIG. 2 illustrates a portion of an aerosol generating system 100 comprising an aerosol generating device 110 and an aerosol generating article 10 according to the embodiment described above and illustrated in FIG. 1.

The aerosol generating device 110 comprises a heating element 120. As shown in FIG. 2, the heating element 120 is mounted within an aerosol generating article receiving chamber of the aerosol generating device 110. In use, the user inserts the aerosol generating article 10 into the aerosol generating article receiving chamber of the aerosol generating device 110 such that the heating element 120 is directly inserted into the aerosol forming substrate 20 of the aerosol generating article 10 as shown in FIG. 2. In the embodiment shown in FIG. 2, the heating element 120 of the aerosol generating device 110 is a heater blade.

The aerosol-generating device 110 comprises a power supply and electronics (shown in FIG. 3) that allow the heating element 120 to be actuated. Such actuation may be manually operated or may occur automatically in response to a user drawing on an aerosol generating article 10 inserted into the aerosol generating article receiving chamber of the aerosol generating device 110. A plurality of openings is provided in the aerosol generating device 110 to allow air to flow to the aerosol generating article 10; the direction of air flow is illustrated by arrows in FIG. 2.

Once the internal heating element 120 is inserted into the aerosol forming substrate 10 of the aerosol generating article 10 and actuated, the aerosol forming substrate 20 of the aerosol generating article 10 is heated to a temperature of approximately 375 degrees Celsius by the heating element 120 of the aerosol generating device 110. At this temperature, volatile compounds are evolved from the aerosol forming substrate 20 of the aerosol generating article 10. As a user draws on the mouth end 70 of the aerosol generating article 10, the volatile compounds evolved from the aerosol forming substrate 20 are drawn downstream through the aerosol generating article 10 and condense to form an aerosol that is drawn through the filter 50 of the aerosol generating article 10 into the user's mouth.

As the aerosol passes downstream thorough the aerosol cooling element 40, the temperature of the aerosol is reduced due to transfer of thermal energy from the aerosol to the aerosol cooling element 40. When the aerosol enters the aerosol cooling element 40, its temperature is approximately 60 degrees Celsius. Due to cooling within the aerosol cooling element 40, the temperature of the aerosol as it exits the aerosol cooling element is approximately 40 degrees Celsius.

Figure 3:
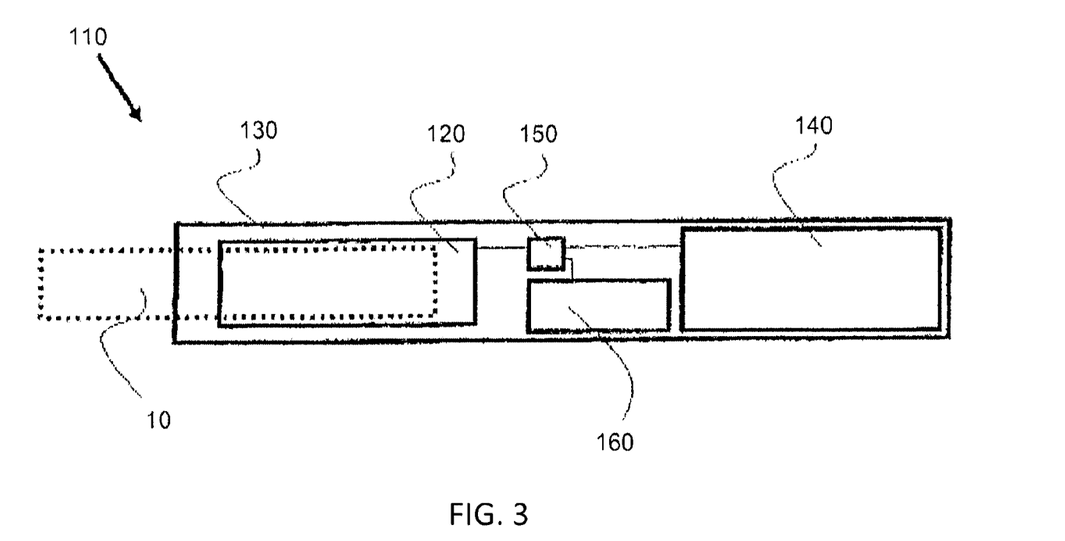
FIG. 3 is a schematic cross-sectional diagram of the electrically heated aerosol generating device illustrated in FIG. 2.

In FIG. 3, components of the aerosol generating device 110 are shown in a simplified manner. Particularly, the components of the aerosol-generating device 110 are not drawn to scale in FIG. 3. Components that are not relevant for the understanding of the embodiment have been omitted to simplify FIG. 3.

As shown in FIG. 3, the aerosol generating device 110 comprises a housing 130. The heating element 120 is mounted within an aerosol generating article receiving chamber within the housing 130. The aerosol generating article 10 (shown by dashed lines in FIG. 3) is inserted into the aerosol generating article receiving chamber within the housing 130 of the aerosol generating device 110 such that the heating element 120 is directly inserted into the aerosol forming substrate 20 of the aerosol generating article 10.

Within the housing 130 there is an electrical energy supply 140, for example a rechargeable lithium ion battery. A controller 150 is connected to the heating element 120, the electrical energy supply 140, and a user interface 160, for example a button or display. The controller 150 controls the power supplied to the heating element 120 to regulate its temperature.

Although the support element of the aerosol generating article according to the embodiment described above and illustrated in FIG. 1 is formed from cellulose acetate, it will be appreciated that this is not essential and that aerosol-generating articles according to other embodiments may comprise support elements formed from other suitable materials or combination of materials.

Similarly, although the aerosol-generating article according to the embodiment described above and illustrated in FIG. 1 comprises an aerosol cooling element comprising a crimped and gathered sheet of polylactic acid, it will be appreciated that this is not essential and that aerosol-generating articles according to other embodiments may comprise other aerosol-cooling elements.

Furthermore, although the aerosol-generating article according to the embodiment described above and illustrated in FIG. 1 has four components circumscribed by an outer wrapper, it will be appreciated than this is not essential and that aerosol generating articles according to other embodiments may comprise additional elements or fewer elements.

It will also be appreciated that while the four components of the aerosol generating article according to the embodiment described above and illustrated in FIG. 1 are circumscribed by an outer wrapper of conventional cigarette paper, this is not essential and that the elements of aerosol generating articles according to other embodiments may be circumscribed by other outer wrappers.

It will further be appreciated that dimensions provided for elements of the aerosol-generating article according to the embodiment described above and illustrated in FIG. 1 and parts of the aerosol generating device according to the embodiment described above and illustrated in FIG. 2 are merely exemplary, and that suitable alternative dimensions may be chosen.

In the following, a non-limiting example is presented which illustrates selective removal of ammonia from aerosol generated by an aerosol generating device.

EXAMPLE

Low ammonia aerosol generating articles ('low articles') and high ammonia aerosol generating articles ('high articles') were prepared for testing. The 'high articles' included a high-Burley blend of tobacco in the aerosol forming substrate. The test articles included acid in either the filter or the cooling element.

Preparation of 'Low Articles'

The low articles were prepared as follows. Briefly, a cellulose acetate filter and a crimped sheet of polylactic acid ("PLA") aerosol cooling element were removed from Philip Morris International HEETS aerosol generating articles. For each of 60 aerosol generating articles, the PLA aerosol cooling element was impregnated with either a 1% (w/v) solution of citric acid in ethanol, a 5% solution of citric acid in ethanol, or pure ethanol (as a reference). The impregnation was accomplished by soaking the PLA elements in the respective solution, placing the soaked elements vertically on filter paper for about 1 min to remove excess solution, and then drying the treated aerosol cooling elements in a vacuum at room temperature for 3 h. The quantities of citric acid added by impregnating the PLA aerosol cooling elements with 1% or 5% citric acid were calculated from the difference of the average weight of these impregnated aerosol cooling elements to the weight of the aerosol cooling elements treated with pure ethanol. The treatment with 1% and 5% citric acid solution resulted in an addition 1.81 and 9.2 mg citric acid per PLA element, respectively. The weight of the PLA element was 2400 mg. Accordingly, the citric acid was incorporated into the element at about 0.08 wt. % and 0.4 wt. %, respectively.

The aerosol generating articles with impregnated filters were prepared by absorbing a droplet of aqueous citric acid solution (0.5 mg in 40 µL) with the upstream end of the filter, drying the treated filters in a vacuum, and reinserting the filters into the aerosol generating articles.

The treated filters or aerosol cooling elements were incorporated into articles having standard (low articles) HEETS aerosol forming substrates.

Preparation of 'High Articles'

The high articles were prepared as follows. Briefly, cellulose acetate filters were removed from Philip Morris International HEETS aerosol generating articles. The filters were impregnated with citric acid by absorbing a droplet of aqueous citric acid solution (1% or 5% citric acid) with the upstream end of the filter, drying the treated filters in a vacuum, and reinserting the filters into the aerosol generating articles. The treatment with 1% and 5% citric acid solution resulted in an addition 0.5 and 1.5 mg citric acid per filter, respectively. The weight of the filter was about 1300 mg. Accordingly, the citric acid was incorporated into the element at about 0.04 wt. % and 0.12 wt. %, respectively.

The treated filters or aerosol cooling elements were incorporated into articles having standard (low articles) HEETS aerosol forming substrates.

Determination of Ammonia and Nicotine Levels in Aerosol

Aerosol levels of ammonia and nicotine were analysed for untreated aerosol generating articles and four different concepts were performed according to ISO 3402:1999, tested under routine cigarette-smoking machine analytical methods as described in ISO 3308:2012, CORESTA recommended method no. 7 for determination of nicotine and CORESTA recommended method no. 79 for determination of ammonia by ion chromatographic analysis.

For the determination of nicotine, trapped aerosol was collected from the test and reference items on a glass fiber filter pad and were extracted using in-situ extraction with 10 ml with isopropanol containing the internal standards n-heptadecane. Nicotine was analyzed by gas chromatography (GC) using flame ionization detection (FID). A gas chromatograph GC Thermo Trace GC Ultra equipped with a computerized data station ('Xcalibur' software), a hydrogen generator $NMH_2$ 160, an autosampler Tri Plus, a DB-Waxeter 15 m×0.32 mm×1.00 μm (Agilent) was used. The content of nicotine was calculated based on a linear regression of a 6-point calibration curve prepared with standard solutions proven by three QC samples. Equipment and analytical conditions employed are shown in Table 1 below.

TABLE 1

Equipment and analytical conditions for nicotine determination

| Equipment | Gas chromatograph GC Thermo Trace GC Ultra |
| --- | --- |
| Software | Xcalibur (2.2 SP1.48) |
| Detector type | flame ionization detection (FID) |
| Detector temperature | 250° C. |
| Analytical column | DB-Waxeter 15 m × 0.32 mm × 1 μm (Agilent) |
| Injection | Split mode |
| Carrier gas flow rate | He 1.8 ml/min |

| Oven temperature program | rate* | temperature [° C.] | hold time [min] |
| --- | --- | --- | --- |
| | — | 150 | 5.50 |
| | 40 | 240 | 1.60 |

For the determination of ammonia, the aerosol generated was collected in two micro impingers, each containing 10 mL of a 0.1 N sulphuric acid ($H_2SO_4$) solution, connected in series behind a glass fibre filter pad. The content of the two micro-impingers, each rinsed with 10 mL of deionized water, was pooled and merged with the pad after smoking and the trapped aerosol collected on the glass fibre filter pad was extracted with the pooled trapping solution. The aerosol extract was analyzed by ion chromatography (IC) using suppressed ion conductivity.

A IC system ICS-50000+ equipped with a temperature controlled autosampler and column heater, a CERS_500_2 mm suppressor, a conductivity detector cation, a computerized data station (Chromeleon) for data acquisition and processing, a column Dionex Ion Pac CS16CG 3×250 mm and a guard column Dionex CG 3×50 mm are used. The content of ammonia is calculated based on a weighted quadratic regression of a 7-point calibration curve prepared proven by two QC samples. Equipment and analytical conditions employed are shown in Table 2 below.

TABLE 2

Equipment and analytical conditions for ammonia determination

| Equipment | ICS-50000 + ICS XEVO TQS |
| --- | --- |
| Software | Chromeleon (7.2.2.6394) |
| Detector type | Conductivity detector (CD) |
| Analytical column | Dionex Ion Pac CS16CG 3 × 250 mm |
| solvent & flow rate | MSA & 0.360 mL/min |
| gradient program | 0 min: 32.00 mM MSA |
| | 11.0 min: 32.00 mM MSA |
| | 11.2 min: 52.00 mM MSA |
| | 15.0 min: 52.00 mM MSA |
| | 15.2 min: 32.00 mM MSA |
| | 22.0 min: 32.00 mM MSA |

Results and Discussion

For the 'Low articles,' significant reductions of ammonia aerosol levels were observed after impregnation of either the PLA aerosol cooling element or the filter with citric acid. Impregnation of the PLA aerosol cooling element with 5% ethanolic citric acid solution resulted in a 34% reduction of aerosol ammonia levels. Impregnation of the PLA aerosol cooling element with 1% citric acid solution and impregnation of the filter with 0.5 mg citric acid both reduced ammonia levels to a similar extent (18 and 20%, respectively) even if impregnation of the PLA aerosol cooling element added a larger amount of acid to the stick (1.81 mg).

Appreciable reductions of nicotine deliveries (5.5%) were observed only for impregnation of PLA aerosol cooling agent with 5% citric acid, indicating that a selective filtration of ammonia from aerosol without affecting nicotine levels is possible. In particular, incorporating an acid on the filter in an article that includes an aerosol cooling agent was shown to have no appreciable nicotine reduction, while exhibiting substantial reduction in ammonia from the aerosol.

Table 1 below provides a summary of the results regarding the removal of ammonia and nicotine from the 'Low articles.'

TABLE 1

Aerosol ammonia and nicotine deliveries of HEETS with or without citric acid impregnation.

| Concept | Ammonia [µg/stick] (mean ± stdev) | Reduction [%] | Nicotine [mg/stick] (mean ± stdev) | Reduction [%] |
|---|---|---|---|---|
| HEETS | 15.12 ± 0.87 | | 1.27 ± 0.04 | |
| HEETS, PLA aerosol cooling element impregnated with citric acid (1.81 mg/stick) | 12.41 ± 0.60 | 18 | 1.26 ± 0.13 | 0.8 |
| HEETS, PLA aerosol cooling element impregnated with citric acid (9.2 mg/stick) | 9.95 ± 0.43 | 34 | 1.20 ± 0.07 | 5.5 |
| HEETS, PLA cooling element treated with pure ethanol | 14.23 ± 0.37 | 6 | 1.27 ± 0.12 | 0.0 |
| HEETS, citric acid on cellulose acetate filter (0.5 mg/stick) | 12.05 ± 0.80 | 20 | 1.27 ± 0.03 | 0.0 |

For the 'High articles,' significant reductions of ammonia aerosol levels were observed after impregnation of the filter with citric acid. Impregnation of the filter with 0.5 mg of citric acid resulted in a 33% reduction of aerosol ammonia levels. Impregnation of the filter with 1.5 mg citric acid reduced ammonia levels resulted in a 60% reduction of aerosol ammonia levels. Nicotine levels were reduced by 6% and 15%, respectively.

Table 2 below provides a summary of the results regarding the removal of ammonia and nicotine from the high-Burley blend aerosol generating articles.

TABLE 2

Aerosol ammonia and nicotine deliveries of HEETS "high-Burley blend" prototypes with or without citric acid impregnation.

| Concept | Ammonia [µg/stick] (mean ± stdev) | Reduction [%] | Nicotine [mg/stick] (mean ± stdev) | Reduction [%] |
|---|---|---|---|---|
| HEETS "high-Burley blend" | 31.2 ± 2.0 | | 1.52 ± 0.19 | |
| HEETS, "high-Burley blend" with citric acid on cellulose acetate filter (0.5 mg/stick) | 21.0 ± 4.6 | 33 | 1.43 ± 0.12 | 6 |
| HEETS, "high-Burley blend" with citric acid on cellulose acetate filter (1.5 mg/stick) | 12.5 ± 0.6 | 60 | 1.28 ± 0.13 | 15 |

All scientific and technical terms used herein have meanings commonly used in the art unless otherwise specified. The definitions provided herein are to facilitate understanding of certain terms used frequently herein.

As used herein, the term "aerosol generating article" is used to denote an article comprising an aerosol forming substrate that is capable of releasing volatile compounds that can form an aerosol. An aerosol generating article may be a non-combustible aerosol generating article, which is an article that releases volatile compounds without the combustion of the aerosol forming substrate. An aerosol generating article may be a heated aerosol generating article, which is an aerosol generating article comprising an aerosol forming substrate that is intended to be heated rather than combusted in order to release volatile compounds that can form an aerosol. A heated aerosol generating article may comprise an onboard heating element forming part of the aerosol generating article, or may be configured to interact with a heating element forming part of a separate aerosol generating device.

An aerosol generating article may be an article that generates an aerosol that is directly inhalable into a user's lungs through the user's mouth. An aerosol generating article may resemble a conventional smoking article, such as a cigarette, and may comprise tobacco. An aerosol generating article may be disposable. An aerosol-generating article may alternatively be partially-reusable and comprise a replenishable or replaceable aerosol forming substrate.

As used herein, the term "aerosol forming substrate" relates to a substrate capable of releasing volatile compounds that can form an aerosol. Such volatile compounds may be released by heating the aerosol forming substrate. An aerosol forming substrate may be adsorbed, coated, impregnated or otherwise loaded onto a carrier or support. An aerosol forming substrate may conveniently be part of an aerosol generating article.

An aerosol forming substrate may comprise nicotine. An aerosol forming substrate may comprise tobacco, for example may comprise a tobacco-containing material containing volatile tobacco flavour compounds, which are released from the aerosol forming substrate upon heating. In preferred embodiments an aerosol forming substrate may comprise homogenised tobacco material, for example cast leaf tobacco.

As used herein, an "aerosol generating device" refers to a device that interacts with an aerosol generating article having an aerosol forming substrate. The device is configured to receive the article and is configured to heat the aerosol forming substrate when the article is received by the device. Preferably, the device is configured to heat the substrate to an extent sufficient to cause the substrate to form an aerosol without combusting the substrate. In other words, the aerosol generating device is preferably a heat-not-burn device. The aerosol generating device may comprise one or more components used to supply energy from a power supply to an aerosol forming substrate to generate an aerosol. For example, the aerosol generating device may comprise a heating element configured to heat the aerosol forming substrate or may comprise components configured to heat a heating element of the aerosol generating article. The heating elements or the components configured to heat a heating element of the aerosol generating article may be operably coupled to a power supply of the aerosol generating device. In addition or alternatively, the aerosol-generating device may be a gas-heated aerosol-generating device. An aerosol generating device may be a smoking device that interacts with an aerosol-forming substrate of an aerosol-generating article to generate an aerosol that is directly inhalable into a user's lungs thorough the user's mouth.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open-ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits under certain circumstances. However, other embodiments may also be preferred under the same or other circumstances. Furthermore, the recitation of one or more preferred embodiments does not imply that other embodiments are not useful, and is not intended to exclude other embodiments from the scope of the disclosure, including the claims.

The embodiments exemplified above are not limiting. Other embodiments consistent with the embodiments described above will be apparent to those skilled in the art. Features described in relation to one embodiment may also be applicable to other embodiments.

The invention claimed is:

1. An aerosol generating article for use with an aerosol generating device, comprising:
    an aerosol forming substrate; and
    an aerosol cooling element downstream of the aerosol forming substrate,
    wherein the aerosol cooling element comprises a body defining a plurality of longitudinally extending channels and an acid in or on the body,
    wherein the cooling element has a porosity of between 50% and 90% in the longitudinal direction.

2. The aerosol generating article according to claim 1, wherein the acid is an organic acid or a phosphoric acid.

3. The aerosol generating article according to claim 1, wherein the acid is selected from the group consisting of malic acid, fumaric acid, succinic acid, citric acid, tartaric acid, ascorbic acid, gluconic acid, lactic acid, a saturated fatty acid having a carbon chain length of at least $C_{12}$, and ortho-phosphoric acid.

4. The aerosol generating article according to claim 1, further comprising a salt of the acid.

5. An aerosol generating article for use with an aerosol generating device, the aerosol generating article comprising:
    an aerosol forming substrate;
    an aerosol cooling element comprising a body defining a plurality of longitudinally extending channels and having a porosity of between 50% and 90% in the longitudinal direction;
    a filter;
    optionally a support element; and
    an acid,
    wherein the aerosol cooling element is downstream of the aerosol forming substrate,
    wherein the filter is downstream of the aerosol forming substrate,
    wherein the support element, if present, abuts the aerosol forming substrate such that the support element is located immediately downstream of the aerosol forming substrate,
    wherein the acid is downstream of the aerosol forming substrate and is positioned to interact with aerosol from the aerosol forming substrate when the aerosol generating article is used with the aerosol generating device, and
    wherein the acid is on the cooling element.

6. The aerosol generating article according to claim 5, wherein the body of the aerosol cooling element comprises polylactic acid.

7. The aerosol generating article according to claim 5, wherein the filter is downstream of the cooling element.

8. The aerosol generating article according to claim 7, wherein the acid is on or in the filter.

9. The aerosol generating article according to claim 7, wherein the filter comprises cellulose acetate tow.

10. The aerosol generating article according to claim 5, wherein the aerosol generating article comprises the support element.

11. The aerosol generating article according to claim 10, wherein the acid is on or in the support element.

12. The aerosol generating article according to claim 5, wherein an amount of ammonia in aerosol delivered by the article when used with the aerosol generating device is reduced by at least 15% relative to a substantially similar aerosol generating article that does not include the acid, and wherein an amount of nicotine in aerosol delivered by the article when used with the aerosol generating device is reduced by 6% or less relative to a substantially similar aerosol generating article that does not include the acid.

13. The aerosol generating article according to claim 5, wherein the aerosol forming substrate comprises tobacco.

14. The aerosol generating article according to claim 5, wherein the acid is an organic acid or a phosphoric acid.

15. The aerosol generating article according to claim 5, wherein the acid is selected from the group consisting of malic acid, fumaric acid, succinic acid, citric acid, tartaric acid, ascorbic acid, gluconic acid, lactic acid, a saturated fatty acid having a carbon chain length of at least $C_{12}$, and ortho-phosphoric acid.

16. The aerosol generating article according to claim 5, further comprising a salt of the acid.

* * * * *